(12) United States Patent
Shalaby

(10) Patent No.: US 7,435,789 B2
(45) Date of Patent: *Oct. 14, 2008

(54) CRYSTALLINE HIGH-COMPLIANCE GLYCOLIDE COPOLYMERS AND APPLICATIONS THEREOF

(75) Inventor: Shalaby W Shalaby, Anderson, SC (US)

(73) Assignee: Poly-Med, Inc., Anderson, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 10/767,975

(22) Filed: Jan. 29, 2004

(65) Prior Publication Data
US 2005/0171299 A1 Aug. 4, 2005

(51) Int. Cl.
*C08G 63/08* (2006.01)
*D02G 3/00* (2006.01)
*B32B 27/06* (2006.01)
*A61L 17/00* (2006.01)

(52) U.S. Cl. ............ 528/354; 525/437; 525/439; 525/450; 428/364; 428/480; 606/230; 606/231

(58) Field of Classification Search ............ 528/354; 525/437, 439, 450; 428/364, 480; 606/230, 606/231
See application file for complete search history.

(56) References Cited

U.S. PATENT DOCUMENTS

| 4,605,730 | A | 8/1986 | Shalaby | |
|---|---|---|---|---|
| 4,700,704 | A | 10/1987 | Jamiolowski | |
| 5,133,739 | A | 7/1992 | Bezwada | |
| 6,255,408 | B1* | 7/2001 | Shalaby | 525/437 |
| 6,494,898 | B1 | 12/2002 | Roby | |
| 6,498,229 | B1* | 12/2002 | Shalaby | 528/302 |
| 6,503,991 | B2* | 1/2003 | Shalaby | 525/437 |
| 6,861,503 | B2* | 3/2005 | Shalaby | 528/425 |
| 7,138,464 | B2* | 11/2006 | Shalaby | 525/411 |
| 2004/0109892 | A1* | 6/2004 | Shalaby | 424/468 |
| 2005/0208096 | A1* | 9/2005 | Shalaby | 424/423 |

* cited by examiner

*Primary Examiner*—Nathan M Nutter
(74) *Attorney, Agent, or Firm*—Leigh P Gregory

(57) ABSTRACT

The present invention is directed toward an absorbable crystalline segmented copolymer comprising a polyalkylene succinate segment end-grafted in a single-step with a mixture of monomers comprising caprolactone, l-lactide, and/or glycolide. The present invention is also directed toward an absorbable crystalline segmented copolymer arising from a trihydroxy compound that is reacted in a single-step with a mixture of monomer comprising ϵ-caprolactone, l-lactide, and/or glycolide to produce monocentric polyaxial polymers.

14 Claims, No Drawings

CRYSTALLINE HIGH-COMPLIANCE GLYCOLIDE COPOLYMERS AND APPLICATIONS THEREOF

FIELD OF THE INVENTION

This invention relates to segmented crystalline copolymers made by one-step copolymerization of a mixture of cyclic monomers comprising glycolide (or l-lactide) and caprolactone using a poly(alkylene succinate)glycol or a trihydroxy compound as the initiator to produce linear or monocentric polyaxial polymers, respectively. The resulting copolymers can be converted to surgical sutures and allied devices.

BACKGROUND OF THE INVENTION

Strategies for the synthesis of crystalline, absorbable, glycolide-based polymers based primarily on glycolide for the production of medical devices that exhibit in-use dimensional stability have been limited to (1) random copolymers with at least 80 percent of their chains derived from glycolide, as in the case of 10:90 poly(l-lactide-co-glycolide), widely used as a braided surgical sutures; (2) random copolymers comprising about 68 to 75 percent glycolide and about 32 to 25 percent, by weight, $\epsilon$-caprolactone to form compliant copolymeric monofilaments having a modulus of about 150 to 250 Kpsi, even though no crystallinity was noted to be present in the copolymer as in U.S. Pat. No. 6,494,898 (2002); (3) segmented/block copolymers which are made by two-step synthesis entailing the preparation of a prepolymer containing a minor fraction of glycolate sequences, followed by end-grafting with glycolide or a mixture of monomers containing more than 80 percent glycolide—the respective general type of chain microstructure and composition was used to prepare highly compliant $\epsilon$-caprolactone/glycolide copolymeric monofilament sutures as in U.S. Pat. No. 4,605,730 (1986), U.S. Pat. No. 4,700,704 (1987), and U.S. Pat. No. 5,133,739 (1992); and (4) segmented block copolymers based on a polyalkylene succinate prepolymer, which is first grafted with trimethylene carbonate and/or $\epsilon$-caprolactone and then grafted further with glycolide, or a glycolide-rich mixture of monomers, to produce copolymers with minimized hydrolytic stability. Monofilament sutures made of these copolymers were claimed to retain their mechanical properties upon aging in a buffered solution at pH 7.4 and 37° C. for longer periods of time as compared with those based on the caprolactone/glycolide copolymers described in statement numbers 1 and 2. However, monofilament sutures made of the copolymers with minimized hydrolytic instability were shown to exhibit less than optimal modulus to produce compliant medical devices such as the sutures disclosed in U.S. Pat. No. 6,255,408 B1 (2001) and U.S. Pat. No. 6,503,991 (2003). In a successful effort to achieve substantial improvement over the prior art disclosed in U.S. Pat. Nos. 4,605,730, 4,700,704, and 5,133,739, a one-step scheme for the synthesis of crystalline, segmented caprolactone/glycolide copolymers and production of compliant absorbable monofilament sutures therefrom was developed as disclosed in U.S. Pat. No. 6,498,229 (2002). However, the breaking strength retention of the monofilament sutures made of these polymers were less than optimal for a short-term, absorbing suture, and a need for new sutures with optimum strength retention profile, without compromising their exceptional compliance, was ascertained. This and the extremely brief breaking strength profile of the monofilament sutures made of the random copolymer of U.S. Pat. No. 6,494,898 (2002) made the need for novel materials more pressing. Accordingly, this invention deals, in part, with novel, absorbable, high glycolide, $\epsilon$-caprolactone copolymers with improved hydrolytic stability and breaking strength retention profile over those of U.S Pat. Nos. 6,498,229 and 6,494,898 without compromising the exceptionally low compliance of the polymers subject of those patents. Furthermore, this invention deals with an improvement on the prior art, wherein the novel copolyesters have superior compliance as compared to the polyalkylene succinate-based crystalline copolymer of minimized hydrolytic instability disclosed in U.S. Pat. Nos. 6,255,408 B1 and 6,503,991. Composition limitations associated with the random copolymer approach and process complexity and fair-to-inadequate reproducibility encountered in the two-step synthesis of segmented glycolide copolymer provided the incentive to explore a simple, and yet reliable, approach to prepare crystalline, high glycolide copolymers with a broad range of physicochemical properties and possibly more than one unique functional performance. Extending the concept of one-step synthesis of segmented crystalline glycolide/caprolactone copolymers based on more than about 80 percent glycolide (e.g., 81 to 95 percent) to produce compliant suture materials appears equally challenging. And this evoked exploring the synthesis of these copolymers in a monocentric polyaxial chain configuration to produce relatively more compliant materials than commercially available, high glycolide, low compliance copolymers such as those based on 90 percent glycolide which is used in producing Vicryl® braided sutures.

SUMMARY OF THE INVENTION

Thus, the present invention is directed to an absorbable segmented crystalline copolymer having a melting temperature of less than 220° C. and a heat of fusion of greater than 10 J/g which is a polyalkylene succinate central segment covalently bonded to crystallizable copolyester segments and is made by a process which involves the steps of providing a poly(alkylene succinate) glycol initiator and end-grafting thereto a cyclic monomer mixture of glycolide and $\epsilon$-caprolactone. In a preferred embodiment the poly(alkylene succinate)glycol is (polyethylene succinate)glycol. For such embodiment preferably the (polyethylene succinate) glycol is at least 1 percent of the total polymerization charge, the remainder is the cyclic monomer mixture, and preferably the mixture is composed of from about 70 percent to about 80 percent by mole of glycolide and from about 30 percent to about 20 percent by mole of caprolactone.

A preferred end-use of the present copolymer is in the form of a monofilament suture having an elastic modulus of less than 300 Kpsi and an ultimate elongation of more than 25 percent. It is preferred that this suture is coated with an absorbable lubricious polymer. A preferred suture is formed from the present inventive copolymer wherein the initiator is poly(ethylene succinate) glycol and wherein the glycolide—caprolactone mixture has a molar ratio of 72:28.

Another preferred end-use of the present copolymer is in the form of a vascular device or part thereof.

In another preferred embodiment the initiator for the present copolymer is poly(trimethylene succinate)glycol. For this embodiment it is preferred that the (polytrimethylene succinate) glycol is at least 1 percent of the total polymerization charge, the remainder is the cyclic monomer mixture, the mixture is composed of from about 70 percent to about 80 percent by mole of glycolide and from about 30 percent to about 20 percent by mole of caprolactone, and the copolymer is in the form of a monofilament suture having an elastic modulus of less than 300 Kpsi and an ultimate elongation of more than 25 percent.

The present invention also is directed to an absorbable segmented crystalline copolymer having a melting temperature of less than 220° C. and a heat of fusion of greater than 10 J/g, which is a polyalkylene succinate central segment covalently bonded to crystallizable copolyester segments and which is made by a process having the steps of providing a poly(alkylene succinate) glycol initiator and end-grafting thereto a cyclic monomer mixture of l-lactide and ε-caprolactone. In a preferred embodiment the poly(alkylene succinate)glycol is poly(ethylene succinate)glycol, the poly(ethylene succinate)glycol is at least one percent of the total polymerization charge, the remainder is the cyclic monomer mixture, and the mixture is composed of from about 75 percent to about 80 percent by mole of l-lactide and from about 25 percent to about 20 percent by mole of caprolactone. This inventive copolymer also may be formed into a monofilament suture having an elastic modulus of less than 300 Kpsi and an ultimate elongation of more than 25 percent. Preferably this suture has a coating of an absorbable lubricious polymer. Another preferred end-use for this inventive copolymer is in the form of a vascular device or part thereof.

The present invention is further directed to an absorbable, monocentric polyaxial segmented crystalline copolymer having a melting temperature of less than 220° C. and a heat of fusion of more than 10 J/g which is made by a process having the steps of providing an initiator which is a monocentric polyhydroxy compound and copolymerizing therewith a mixture of ε-caprolactone and a second monomer such as glycolide, l-lactide, or a morpholine-2,5-dione. In a preferred embodiment the initiator is trimethylolpropane, the second monomer is glycolide, and the glycolide comprises from about 70 to about 80 percent by mole of the mixture and the caprolactone comprises from about 30 to about 20 percent by mole of the mixture. A preferred end use for this copolymer is in the form of a coated monofilament suture having an elastic modulus of less than 300 Kpsi wherein the coating is an absorbable polymer. In another preferred embodiment the initiator is trimethylolpropane, the second monomer is lactide, and the lactide comprises from about 70 to about 80 percent by mole of the mixture and the caprolactone comprises from about 30 to about 20 percent by mole of the mixture. For this embodiment, a preferred end use is in the form of a coated monofilament suture having an elastic modulus of less than 300 Kpsi, wherein the coating is an absorbable polymer.

In another preferred embodiment the initiator is trimethylolpropane, the second monomer is glycolide, and the glycolide comprises from about 81 to about 95 percent by mole of the mixture and the caprolactone comprises from about 19 to about 5 percent by mole of the mixture. For this embodiment a preferred end use is in the form of a coated multifilament braided suture wherein the coating is an absorbable polymer. Another preferred end use for this embodiment is in the form of multifilament yarn constructed into a vascular device or part thereof.

DETAILED DESCRIPTION OF PREFERRED EMBODIMENTS

The present invention is directed to absorbable crystalline segmented copolymers having a melting temperature of less than about 220° C. and heat of fusion of more than 10 J/g, comprising a polyalkylene succinate central segment end-grafted in a single-step with a mixture of cyclic monomers comprising glycolide and caprolactone. According to one aspect of the invention, the crystalline segmented copolymer is made by end-grafting poly(ethylene succinate)glycol or poly(trimethylene succinate)glycol [poly(1,3-propylene succinate)glycol], as a dihydroxy initiator, with a mixture of glycolide and caprolactone in one-step in the presence of stannous octanoate as the catalyst using a reaction temperature of about 180° C. or less. Another aspect of this invention deals with end-grafting poly(alkylene succinate)glycol with a mixture of l-lactide and caprolactone. A specific aspect of this invention deals with the use of poly(ethylene succinate)glycol or poly(trimethylene succinate)glycol as a difunctional initiator, at a level of at least one percent by weight, for one-step end-grafting with a mixture of cyclic monomers comprising glycolide and ε-caprolactone at molar ratios of 65:35 to 80:20. Another specific aspect of the invention deals with the use of poly(ethylene succinate)glycol or poly(trimethylene succinate)glycol [poly(1,3-propylene succinate)glycol] as a difunctional initiator, at a level of at least one percent by weight, for one-step end-grafting with a mixture of cyclic monomers comprising l-lactide and ε-caprolactone at molar ratios of 70:30 to 90:10. Another aspect of this invention deals with the use of poly(ethylene succinate)glycol or poly(trimethylene succinate)glycol for end-grafting with a mixture of cyclic monomer comprising glycolide, caprolactone, and a third monomer such as l-lactide, trimethylene carbonate, 1,5-dioxepan-2-one, and p-dioxanone wherein the molar ratios of the glycolide:caprolactone:third monomer varies from 80:16:4 to 70:25:5, but preferably 78:19:3 and more preferably 78:20:2. Another aspect of this invention deals with a copolymer, made by one-step end-grafting of a poly(ethylene succinate)glycol or poly(trimethylene succinate)glycol with a mixture of monomers comprising glycolide and ε-caprolactone, in the form of a monofilament suture having an elastic modulus of less than 300 Kpsi and an ultimate elongation of more than 25 percent, but preferably a monofilament suture having an elastic modulus of less than 200 Kpsi and ultimate elongation of more than 40, and more preferably a monofilament suture having an elastic modulus of less than 140 Kpsi and ultimate elongation of more than 50 percent. Another aspect of this invention deals with a copolymer, made by one-step end-grafting of a poly(ethylene succinate)glycol or poly(trimethylene succinate)glycol with a mixture of cyclic monomer comprising glycolide and caprolactone, in the form of a monofilament suture coated with less than 1.5 percent, but preferably less than one percent of an absorbable lubricious polymeric coating having chain sequences comprising those derived from caprolactone and glycolide. It is also preferred that such coating is made by the copolymerization of caprolactone and glycolide in the presence of glycolic acid as the initiator to produce a carboxy-terminated copolyester that can be partially neutralized with a basic amino acid, such as lysine or arginine, to achieve autocatalyzed hydrolysis of the copolyester in the biologic environment. The suture coating can be also made by the copolymerization of glycolide and caprolactone in the presence of a basic initiator, such as triethanolamine. Another aspect of this invention deals with the segmented crystalline copolymer described above and comprising a polyalkylene succinate central segment in the form of a vascular device.

Another aspect of this invention deals with segmented crystalline copolymers made by the one-step copolymerization of a mixture of cyclic monomers comprising glycolide and caprolactone at molar ratios that vary below about 81:19 to 95:5 in the presence of a trihydroxy compound having a molecular weight of less than 300 Da, such as trimethylolpropane and triethanolamine to produce monocentric polyaxial (triaxial) crystalline segmented copolymers having a melting temperature of less than 220° C. and heat of fusion of more than 10 J/g. The resulting monocentric polyaxial (triaxial) copolymers can be used in the production of (1) braided multifilament sutures with complaint, single filaments having relatively lower intrinsic modulus (or higher compliance) and higher breaking strength profile in the biological environment as compared to those of the most commonly used absorbable sutures, namely the Vicryl® braid that is based on 90/10 glycolide/l-lactide copolymer; (2) monofilament sutures with superior breaking strength profile while being more compliant as compared to those made from linear block copolymers of glycolide and trimethylene carbonate; and (3) simple or composite textile constructs, such as those used in vascular devices, which can be fully or partially absorbable. The monocentric polyaxial configuration of these copolymers contributes to (1) the improved hydrolytic stability and hence, breaking strength retention profile of the resulting sutures; and (2) a unique crystallization mode that is responsible for lowering the sutures' intrinsic modulus.

The monofilament and braided sutures derived from monocentric polyaxial glycolide/caprolactone made by single-step copolymerization can be coated with the same coating described above for sutures based on end-grafted poly(alkylene succinate)glycol. The coating add-on may not exceed 1.5 and 10 percent for the monofilament and braided sutures, respectively.

This invention also deals with segmented crystalline copolymers made by one-step copolymerization of a mixture of ε-caprolactone and a substituted or unsubstituted morpholine-2,5-dione with glycolide or lactide using a poly(alkylene succinate)glycol or a monocentric polyhydroxy compound, such as trimethylolpropane as an initiator to produce linear or monocentric copolymers, respectively, useful for the production of monofilament sutures, multifilament braided sutures, and multifilament yearn in the form of vascular devices or parts thereof. Typical monomeric mixtures of those noted above may comprise l-lactide, a morpholine-2,5-dione, and ε-caprolactone in molar ratios of 81:3:16 to 85:4:11. Substituting l-lactide as the main component of the latter mixtures can be used to produce copolymers associated with the molar ratios of 81:1:18 to 89:1:10 glycolide, morpholine-2,5-dione and caprolactone.

This invention is also directed to a vascular device or part of a vascular device made of a multifilament yarn and based on a monocentric polyaxial segmented crystalline copolymer made by one-step copolymerization of a mixture of glycolide or lactide with caprolactone at molar ratios of about 81:19 to 95:5 in the presence of a monocentric polyhydroxy initiator such as trimethylolpropane and triethanolamine. In another aspect of this invention, the preceding monomeric mixture may consist of l-lactide, a morpholine-2,5-dione, and caprolactone at molar ratios of about 81:3:16 to 85:4:11. The multifilament yarn described above can be used in producing multifilament braided sutures, vascular devices, and/or parts of vascular devices. This invention deals, in part, with an absorbable, high-compliance, segmented crystalline, copolymer with melting temperature of less than 220° C. and heat of fusion ($\Delta H_f$) of more than 10 J/g, a modulus of elasticity in a fiber form of less than 300 Kpsi, and can be made by direct, one-step copolymerization at or below about 180° C. using about 65 to 80 molar parts of l-lactide and/or glycolide and about 30 to 20 molar parts of ε-caprolactone in the presence of a low molecular weight poly(alkylene succinate)glycol (i.e., hydroxy-terminated polyalkylene succinate) as the initiator and an organo-tin compound as the catalyst; this is to produce linear segmented crystalline polymers. One specific aspect of this invention deals with a crystalline copolymer suitable for the production of a monofilament suture made by the copolymerization of a mixture of glycolide/caprolactone at molar ratios from about 70:30 to about 80:20 in the presence of a poly(alkylene succinate)glycol such as poly(ethylene succinate)glycol or poly(trimethylene succinate)glycol as an initiator and stannous octoate as the catalyst. One more specific aspect of this invention deals with a crystalline, high-compliance copolymer made by the direct copolymerization of a mixture of glycolide and caprolactone at molar ratios from about 70:30 to 80:20 in the presence of poly(ethylene succinate)glycol as the initiator in amounts exceeding one percent of the total weight of the polymerization charge. Another aspect of this invention deals with a high-compliance, crystalline copolymer made by the direct polymerization of l-lactide and caprolactone at molar ratios from about 70:30 to about 80:20 in the presence of a poly(ethylene succinate) glycol as the initiator in amounts exceeding one percent of the total weight of the polymerization charge. Another specific aspect of this invention deals with an absorbable, high-compliance, crystalline copolymer made by the direct copolymerization of a mixture of l-lactide, glycolide, and ε-caprolactone at molar ratios of about 82:2:16 to about 89:1:10, respectively, in the presence of a poly(ethylene succinate)glycol as the initiator in an amount exceeding one percent of the total weight of the polymerization charge.

Another key aspect of this invention deals with the direct one-step copolymerization of a mixture of cyclic monomers comprising two or more members of the group represented by glycolide, l-lactide, ε-caprolactone, p-dioxanone, 1,5-dioxepan-2-one, morpholine-2,5-dione, gem-dimethyl morpholine-2,5-dione, and trimethylene carbonate in the presence of a polyhydroxy compound with a central atom as an initiator having a molecular weight of less than 300 Da, to produce monocentric polyaxial copolymers. The concept of constructing a monocentric polyaxial chain (a chain with a central atom and more than two branches) as in the case of a triaxial chain (chain with a central atom and three practically equal length branches) is conceived as a means to reduce crystallizability, overall crystallinity, and crystallite size of the crystalline fraction of the polymer as a result of the imposed, controlled chain branching. This, in turn, leads to lowering the degree of crystallinity, decreasing the polymer modulus (or increasing its compliance). In addition, having a triaxial chain with three load-bearing branches decreases the effect of chain scission during hydrolytic degradation leading to a prolonged breaking strength retention profile. A specific aspect of this invention deals with a high-compliance, crystalline polymer made by the direct, one-step copolymerization of a mixture of glycolide and caprolactone at molar ratios from about 70:30 to 80:20 in the presence of a polyhydroxy compound with a molecular weight of less than 300 Da, such as triethanolamine and trimethylol propane to produce a monocentric polyaxial and specifically triaxial polymer. Another specific aspect of this invention deals with a high-compliance, monocentric polyaxial and, specifically, a triaxial crystalline polymer made by the direct copolymerization of a mixture of l-lactide and caprolactone at molar ratios of about 70:30 to about 80:20 in the presence of polyhydroxy compound having a molecular weight of less than 300 Da, such as triethanolamine and trimethylol propane, as the initiator to produce a monocentric polyaxial and, specifically, triaxial copolymer. Another specific aspect of this invention deals with a high-compliance, crystalline polymer made by the direct, one-step copolymerization of a mixture of l-lactide, glycolide, and caprolactone at the respective molar ratios of about 70:5:25 to about 85:2:13 in the presence of a polyhydroxy compound having a molecular weight of less than 300 Da, such as triethanol amine and trimethylol propane as the initiator to produce triaxial copolymers. Another specific aspect of this invention deals with compliant, absorbable monofilament sutures having an elastic modulus of less than 300 Kpsi and preferably less than 200 Kpsi and more preferably less than 100 Kpsi made from one of the triaxial copolymers described above and preferably one of those made of glycolide and ε-caprolactone at molar ratios of about 70:30 to 80:20. Another specific aspect of this invention deals braided suture precursors based on high-lactide or high-glycolide monocentric polyaxial copolymers. A more specific aspect of this invention deals with a monocentric polyaxial copolymer made by the one-step copolymerization of glycolide and ε-caprolactone at molar ratios of about 81:19 to 95:5 in the presence of trimethylol propane or triethanolamine as the initiator and stannous octanoate as the catalyst, for use in the production of multifilament braided sutures that are preferably coated with an absorbable polymer. Another more specific aspect of this invention deals with monocentric polyaxial copolymers made by the one-step copolymerization of l-lactide and ε-caprolactone at molar ratios between about 85:15 and 95:5 in the presence of trimethylol propane as the initiator for the use in the production of multifilament braided sutures, coated with an absorbable copolyester. The resulting monocentric polyaxial (triaxial) copolymers can be used in the production of (1) braided multifilament sutures with complaint, single filaments having relatively lower intrinsic modulus (or higher compliance) and higher breaking strength profile in the biological environment as compared to those of the most commonly used absorbable sutures, namely the Vicryl® braid that is based on 90/10 glycolide/l-lactide copolymer; (2) monofilament sutures with superior breaking strength profile while being more compliant as compared to those made from linear block copolymers of glycolide and trimethylene carbonate; and (3) simple or composite textile constructs, such as those used in vascular devices, which can be fully or partially absorbable. The monocentric polyaxial configuration of these copolymers contributes to (1) the improved hydrolytic stability and hence, breaking strength retention profile of the resulting sutures; and (2) a unique crystallization mode that is responsible for lowering the sutures' intrinsic modulus.

The monofilament and braided sutures derived from monocentric polyaxial glycolide/caprolactone made by single-step copolymerization can be coated with the same coating described above for sutures based on end-grafted poly(alkylene succinate)glycol. The coating add-on may not exceed 1.5 and 10 percent for the monofilament and braided sutures, respectively.

This invention also deals with segmented crystalline copolymers made by one-step copolymerization of a mixture of ε-caprolactone and a substituted or unsubstituted morpholine-2,5-dione with glycolide or lactide using a poly(alkylene succinate)glycol or a monocentric polyhydroxy compound, such as trimethylolpropane as an initiator to produce linear or monocentric copolymers, respectively, useful for the production of monofilament sutures, multifilament braided sutures, and multifilament yearn in the form of a vascular device or parts thereof. Typical monomeric mixtures of those noted above may comprise l-lactide, a morpholine-2,5-dione, and ε-caprolactone in molar ratios of 81:3:16 to 85:4:11. Substituting l-lactide as the main component of the latter mixtures with glycolide can be used to produce copolymers associated with the molar ratios of 81:1:18 to 89:1:10 glycolide, morpholine-2,5-dione and caprolactone.

This invention is also directed to a vascular device or part of a vascular device made of a multifilament yarn and based on a monocentric polyaxial segmented crystalline copolymer made by one-step copolymerization of a mixture of glycolide or lactide with caprolactone at molar ratios of about 81:19 to 95:5 in the presence of a monocentric polyhydroxy initiator such as trimethylolpropane and triethanolamine. In another aspect of this invention, the preceding monomeric mixture may consist of l-lactide, a morpholine-2,5-dione, and caprolactone at molar ratios of about 81:3:16 to 85:4:11. The multifilament yarn described above can be used in producing multifilament braided sutures, vascular devices, and/or parts of vascular devices.

A specific aspect of this invention deals with an absorbable medical device made of one or more of the copolymer of the present invention. A more specific aspect of this invention deals with a vascular device, such as a femoral artery plugging device, made of one or more of the copolymer described subject of this invention. Another more specific aspect of this invention deals with a compliant monofilament suture made of one of the copolymers subject of this invention. Another aspect of the present invention is the use of the subject polymer as a flexible backing for chitosan and acylated chitosan in the form of microporous, foam, non-woven fabrics and electrospun fabrics for use as a pad for vascular applications, and particularly vascular wraps or patches and hemostatic bandages. Such devices may also contain bioactive agents such as antimicrobial compounds, growth promoting factors, and hemostatic drugs.

Additional illustrations of the present invention are provided by the following specific examples:

EXAMPLE 1

Preparation of Poly(ethylene succinate)glycol (PESG-1A)

In a predried reactor equipped for mechanical stirring, ethylene glycol (5.94 mole, 368.8 g) and diethylsuccinate (2.48 mole, 431.2 g) and a catalytic amount of dibutyltin oxide (0.3094 mmole, 77 mg) were heated gradually under atmospheric nitrogen from room temperature to 185° C. to distil volatile by-products after implementing to the following scheme: 185° C./1 hr, 195° C./1 hr, 205° C./1 hr, and 215° C./1 hr. The reactants were then cooled to room temperature and heated under reduced pressure (<0.5 mm Hg) from room temperature to 165° C. and continued according to the following scheme: 165° C./3 hrs and 180° C./1.5 hrs. At the conclusion of the polymerization, the product was cooled, isolated, and then analyzed for identity using IR and NMR and for molecular weight using GPC in dichloromethane. The latter method revealed an $M_n$=2970 Da for Lot A (PESG-1A). Two additional lots, PESG-1B and PESG-1C, were prepared using slightly extended post-polymerization periods to achieve $M_n$ of 3000 and 3300 Da, respectively.

EXAMPLE 2

Preparation of Poly(ethylene succinate)glycol (PESG-2)

This was prepared under conditions similar to those used in preparing PESG-1 in Example 1, with the exception of extending the post-polymerization period at 180° C. Accordingly, the latter step was extended beyond 1.5 hours until a molecular weight of 5310 Da was achieved (as determined by GPC).

EXAMPLE 3

Preparation of Poly-1,3-propylene Succinate Glycol (PPSG-1)

This was prepared from 1,3-propylene glycol and diethyl succinate under conditions similar to those used in preparing PESG-1 in Example 1, with the exception of extending the post-polymerization period at 180° C. Accordingly, the latter was extended beyond 2.5 hours until a molecular weight of 8290 Da was achieved.

EXAMPLE 4

Direct Conversion of 70:30 Mixture of Glycolide/ε-Caprolactone into Segmented Copolymer Using Poly(ethylene succinate)glycol (PESG-1A) as Initiator In a predried reactor equipped for mechanical stirring, glycolide (3.6395 mole, 422.2 g), caprolactone (1.5598 mole, 177.8 g), and PESG-1A from Example 1 (5.1993×10$^{-3}$ mole, 15.4 g) were heated to 95° C. for 25 minutes to melt the monomer and a catalytic amount of stannous octoate (1.4855×10$^{-3}$ mole as a 0.2 M solution in toluene) was then added under dry nitrogen atmosphere. The polymerization was then conducted at 180° C. for 7 hr. At the conclusion of the polymerization, the polymer melt was cooled, the solid product was isolated, and ground. The ground polymer was heated under reduced pressure (<0.5 mm H$_g$) to remove unreacted monomer. The purified polymer was characterized for identity by IR, thermal properties by DSC, and molecular weight in terms of inherent viscosity (I.V.) in hexafluoro-2-propanol. Accordingly, the polymer exhibited a T$_m$=175° C., ΔH$_f$=36 J/g, I.V.=2.25 dL/g.

EXAMPLE 5

Direct Conversion of 72/28 Mixture of Glycolide/ε-Caprolactone into Segmented Copolymer Using Poly(ethylene succinate)glycol (PESG-2) as Initiator The polymerization was conducted under conditions similar to those used in Example 4, with the exception of using the following charges of reactants and catalyst:
PESG-2 (M$_n$=5310 Da), 21 g
Glycolide (708.3 g, 6.106 moles)
ε-Caprolactone (270.7 g, 2.3746 moles)
Stannous Octanoate 0.2M solution in Toluene (1.212 mL, 2.423×10$^{-4}$ moles)
The final product was shown to have an inherent viscosity (in HFIP) of 1.4 dL/g, T$_m$=186° C., and ΔH$_f$=53.9 J/g.

EXAMPLE 6

Direct Conversion of a 76/24 Mixture of Glycolide/ε-Caprolactone into Segmented Copolymer Using Poly(ethylene succinate)glycol, PESG-1A, as Initiator The polymerization was conducted under conditions similar to those used in Example 4, with the exception of using the following charges of reactants and catalyst:
PESG-1A (M$_n$=2790 Da), 12.9 g
Glycolide (457.9 g, 3.9474 moles)
ε-Caprolactone (142.6 g, 1.25 moles)
Stannous Octanoate 0.2M solution in Toluene (0.743 mL, 1.486×10$^{-4}$ moles)
The final product was shown to have an inherent viscosity (in HFIP) of 1.12 dL/g, T$_m$=191° C., and ΔH$_f$=44 J/g.

EXAMPLE 7

Direct Conversion of a 72/28 Glycolide/ε-Caprolactone Mixture into Segmented a Copolymer Using Poly-1,3-propylene Succinate Glycol, PPSG-1

The polymerization was conducted under conditions similar to those used in Example 4, with the exception of using the following charges of reactants and catalyst:
PPSG-1 (M$_n$=8290 Da), 24 g
Glycolide (416.9 g, 3.5925 moles)
ε-Caprolactone (159.3 g, 1.3971 moles)
Stannous Octanoate 0.2M solution in Toluene (0.713 mL, 1.426×10$^{-4}$ moles)
The final product was shown to have an inherent viscosity (in HFIP) of 1.12 dL/g, T$_m$=179° C., and ΔH$_f$=40 J/g.

EXAMPLE 8

Direct Conversion of a Mixture of 75/25 Glycolide/ε-Caprolactone into a Segmented Copolymer Using Poly(ethylene succinate)glycol, PESG-1,C as Initiator This polymerization was conducted under conditions similar to those used in Example 4 with the exception of using 9 hours at 180° C. and the following charge of reactants and catalyst:
PESG-1C (M$_n$=3330 Da), 16.9 g
Glycolide (590.3 g, 5.09 moles)
ε-Caprolactone (193.8 g, 1.7 moles)
Stannous Octanoate 0.2M solution in Toluene (0.97 mL, 1.94×10$^{-4}$ moles)
The final product was shown to have an inherent viscosity (in HFIP) of 1.11 dL/g, T$_m$=192° C., and ΔH$_f$=44 J/g.

EXAMPLE 9

Direct Conversion of a Mixture of 66:34 Glycolide/ε-Caprolactone into a Segmented Copolymer Using Polyethylene Succinate, Glycol PESG-1B, as Initiator The polymerization was conducted under conditions similar to those used in Example 4, with the exception of using the following charges of reactants and catalysts:
PESG-1B (M$_n$=3000 Da), 12.6 g
Glycolide (390.3 g, 3.365 moles)
ε-Caprolactone (197.3 g, 1.73 moles)
Stannous Octanoate 0.2M solution in Toluene (0.728 mL, 1.456×10$^{-4}$ moles)
The final product was shown to have an inherent viscosity (in HFIP) of 1.25 dL/g, T$_m$=139° C., and ΔH$_f$=32 J/g.

EXAMPLE 10

General Method of Converting a Typical Polymer to a Monofilament Suture and Properties Thereof Purified, dried polymer granules from Example 4 were mixed with D & C violet #2 (at 0.05% by weight) and melt extruded using a ¾", single-screw extruder with one-hole die. Using an average melt temperature of 220° C. and die temperature of 225° C., monofilament yarn was extruded into the desired size. The extrudates were oriented by drawing in two stages at 80 and 105° C. for total draw ratio of 6×. The drawn monofilaments were relaxed at 60-80° C. for 10 to 20 minutes to reduce their free shrinkage to less than 2% at 60° C. The monofilaments were then tested for pertinent suture properties and exhibited the following properties:

| | |
|---|---|
| Diameter: | 0.28 mm |
| Knot Strength: | 23 N |
| Linear Breaking Strength: | 32 N |
| Elastic Modulus: | 52 Kpsi |
| Elongation: | 65% |

EXAMPLE 11

Preparation of Absorbable Coating Polymer (CP)

Following a similar method to those described in U.S. Pat. No. 5,773,561 (1998), the coating polymer, CP, was prepared using glycolide (73.2 g), ε-caprolactone (1369.8 g), glycolic acid (91.2 g), and stannous octoate (3 mL of 0.8 M solution in toluene). Accordingly, the polymerization was conducted primarily by heating at 150° C. under dry nitrogen atmosphere for 14 hours. The product was characterized for identity (IR), composition (NMR), and melting transition (DSC).

EXAMPLE 12

Preparation of the CP Coating Solution and Application to a Typical Monofilament Suture This entailed preparing the lysine salt of the coating polymer, CP, in acetone using less than the stoichiometric amount of the lysine to neutralize the acid end-group of the CP, as described in U.S. Pat. No. 5,773,561 (1998). The concentration of the acetone solution of the CP-lysine salt was adjusted to allow for a final coating add-on on the coated suture of less than 1 percent. The coating process entailed continuous threading of the monofilament through the coating bath at 25° C. The exiting coated suture was immediately passed through a drying chamber to remove the acetone from the applied coating.

EXAMPLE 13

Processing of Additional Specific Polymers into Monofilaments and Suture Properties Thereof Three polymers, made according to Examples 4, 5, and 7, were extruded/oriented into drawn monofilament sutures as described in Table I. The monofilament sutures were coated as in Example 12, tested for their suture properties in terms of their mechanical properties and in vivo breaking strength retention (BSR) as outlined in Table I. The percent BSR was determined by (1) implanting, subcutaneously, the ethylene-oxide, sterilized sutures in rats; (2) retrieving the sutures at one week; (3) determining the breading strength or maximum load; and (4) dividing the maximum load at one week by the initial one and multiplying by 100.

aspects of the various embodiments may be interchanged in whole or in part. Therefore, the spirit and scope of the appended claims should not be limited to descriptions and examples herein.

What is claimed is:

1. An absorbable, compliant monofilament exhibiting a modulus of less than 100 kpsi and comprising a segmented crystalline copolymer having a melting temperature of less than 220° C. and heat of fusion greater than 10 J/g, the copolymer made by the process comprising the single step of end-grafting a cyclic monomer mixture comprising glycolide and ε-caprolactone to a poly(alkylene succinate) glycol initiator.

2. A monofilament as set forth in claim 1 wherein the poly(alkylene succinate)glycol comprises (polyethylene succinate)glycol.

3. A monofilament as set forth in claim 2 wherein the (polyethylene succinate) glycol comprises at least 1 percent of the total polymerization charge, the remainder comprising the cyclic monomer mixture, and wherein the mixture comprises from about 70 percent to about 80 percent by mole of glycolide and from about 30 percent to about 20 percent by mole of caprolactone.

4. A monofilament as set forth in claim 1 in the form of a suture, the monofilament suture having an ultimate elongation of more than 25 percent.

5. A monofilament as set forth in claim 4 wherein the suture is coated with an absorbable lubricious polymer.

6. A monofilament as set forth in claim 5 wherein the poly(alkylene succinate) glycol initiator comprises poly(ethylene succinate) glycol and wherein the glycolide-caprolactone mixture comprises a molar ratio of 72:28.

7. A monofilament as set forth in claim 1 as part of a vascular device.

8. An absorbable, compliant monofilament exhibiting a modulus of less than 100 kpsi and comprising a segmented crystalline copolymer having a melting temperature of less than 220° C. and heat of fusion greater than 10 J/g, the copolymer made by a process comprising the single step of end-grafting a cyclic monomer mixture comprising l-lactide and ε-caprolactone to a poly(alkylene succinate) glycol initiator.

TABLE I

Processing of Specific Polymers into Drawn Monofilaments

| | Extrusion Temperatures | | Orientation Condition* | | Mechanical Properties | | | | In vivo BSR, |
|---|---|---|---|---|---|---|---|---|---|
| Polymer Source | Melt, ° C. | Die, ° C. | Temp., ° C. | Draw Ratio | Diam., mm | Max. Load N, Kpsi | Modulus, Kpsi | Elong., % | %, @ 1 Week |
| Example 4 | 198 | 215 | 80-105 | 6 X | 0.29 | 28.6, (62) | 49 | 65 | 63 |
| Example 5 | 189 | 219 | 85-125 | 4.5 X | 0.21 | 17.6, (75.4) | 74.6 | 74.5 | 60.7 |
| Example 7 | 197 | 211 | 85-105 | 5.5 X | 0.39 | 54.5, (66.9) | 35 | 65 | — |

*Two-stage drawing.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that 9. A monofilament as set forth in claim 8 wherein the poly(alkylene succinate)glycol initiator comprises poly(ethylene succinate)glycol, the poly(ethylene succinate) glycol comprising at least one percent of the total polymerization charge, the remainder comprising the cyclic monomer mixture, the mixture comprising from about 75 percent to about 80 percent by mole of l-lactide and from about 25 percent to about 20 percent by mole of caprolactone.

10. A monofilament as set forth in claim 9 in the form of a suture, the monofilament suture having an ultimate elongation of more than 25 percent.

11. A monofilament as set forth in claim 10 further comprising a coating comprising an absorbable lubricious polymer.

12. A monofilament as set forth in claim 9 as part of a vascular device.

13. A monofilament as set forth in claim 1 wherein the poly(alkylene succinate)glycol initiator comprises poly(trimethylene succinate)glycol.

14. A monofilament as set forth in claim 13 wherein the (polytrimethylene succinate) glycol comprises at least 1 percent of the total polymerization charge, the remainder comprising the cyclic monomer mixture, wherein the mixture comprises from about 70 percent to about 80 percent by mole of glycolide and from about 30 percent to about 20 percent by mole of caprolactone, and wherein the monofilament is in the form of a monofilament suture having an ultimate elongation of more than 25 percent.

* * * * *